United States Patent [19]
Friedman et al.

[11] Patent Number: 5,514,670
[45] Date of Patent: May 7, 1996

[54] SUBMICRON EMULSIONS FOR DELIVERY OF PEPTIDES

[75] Inventors: Doron Friedman, Carmei Yosef; Joseph Schwarz; Shimon Amselem, both of Rehovot, all of Israel

[73] Assignee: Pharmos Corporation, New York, N.Y.

[21] Appl. No.: 106,107

[22] Filed: Aug. 13, 1993

[51] Int. Cl.$^6$ .......................... A01N 37/18; A61K 31/74; A61K 38/16; A61K 38/00

[52] U.S. Cl. .................. 514/2; 514/3; 514/8; 514/11; 514/12; 514/13; 514/14; 514/15; 514/18; 514/19; 424/78.08; 424/78.31; 424/78.33

[58] Field of Search .................. 514/2, 3, 8, 11, 514/12, 13, 14, 15, 18, 19; 424/78.08, 78.31, 78.33

[56] References Cited

U.S. PATENT DOCUMENTS

| | | | |
|---|---|---|---|
| 3,919,411 | 11/1975 | Glass et al. | 424/81 |
| 4,548,922 | 11/1985 | Carey et al. | 514/4 |
| 5,055,303 | 10/1991 | Riley, Jr. | 424/436 |
| 5,120,710 | 6/1992 | Liedtke | 514/3 |
| 5,188,837 | 2/1993 | Domb | 424/450 |
| 5,206,219 | 4/1993 | Desai | 514/3 |

FOREIGN PATENT DOCUMENTS

| | | |
|---|---|---|
| 0115627 | 12/1983 | European Pat. Off. . |
| 0140085 | 9/1984 | European Pat. Off. . |
| 0442671A2 | 2/1991 | European Pat. Off. . |
| 0494654A2 | 1/1992 | European Pat. Off. . |
| 2127689 | 8/1983 | United Kingdom . |
| WO90/03164 | 4/1990 | WIPO . |
| WO91/05545 | 5/1991 | WIPO . |
| WO91/14454 | 10/1991 | WIPO . |
| WO92/03121 | 3/1992 | WIPO . |
| WO92/18147 | 10/1992 | WIPO . |
| WO93/00077 | 1/1993 | WIPO . |
| WO93/00076 | 1/1993 | WIPO . |
| WO94/03157 | 2/1994 | WIPO . |

OTHER PUBLICATIONS

J. Pharm. Pharmacol, 1992, 44 (Suppl. 1): 186–190, "Delivery Systems for Biopharmaceuticals", by S. S. Davis.

Meth Find Exp Clin Pharmacol. 1991, 13(3): 205–220, "Microemulsions for Improved Peptide Absorption from the Gastrointestinal Tract", by W. A. Ritschel.

The United States Pharmacopeia, The National Formulary, XXth Edition 1990, pp. 1910–1912.

Deutscher, Guide to Protein Purificaiton, Academic Press, 1990 pp. 77–78.

*Primary Examiner*—Jill Warden
*Assistant Examiner*—Benet Prickril
*Attorney, Agent, or Firm*—Pennie & Edmonds

[57] ABSTRACT

The present invention provides emulsions comprising a plurality of submicron particles, a bioactive peptide, and an aqueous continuous phase or that effect enhanced oral bioavailability of the peptide. Another aspect of the invention provides compositions and methods of administering peptides in an emulsion comprising a plurality of submicron particles, a mucoadhesive macromolecule, a bioactive peptide, and an aqueous continuous phase, which promotes absorption of the bioactive peptide through mucosal surfaces by achieving mucoadhesion of the emulsion particles. Mucous surfaces suitable for application of the emulsions of the present invention may include corneal, conjunctival, buccal, sublingual, nasal, vaginal, pulmonary, stomachic, intestinal, and rectal routes of administration.

39 Claims, 5 Drawing Sheets

SUBMICRON EMULSIONS FOR DELIVERY OF PEPTIDES

1. FIELD OF THE INVENTION

The present invention relates to lipid-in-water emulsions for the administration of peptides, and to methods and compositions for enhancing the absorption of such peptides across mucosal membranes.

2. BACKGROUND OF THE INVENTION

A well-known problem with the administration of peptides is that they are susceptible to acid hydrolysis and enzymatic degradation when administered orally. For this reason, parenteral administration has been the most widely used method; in the case of peptides of higher molecular weight, the parenteral route has provided the only effective means of administration. However, administration by injection is both inconvenient and unpleasant for the patient, particularly when injections must be repeated regularly over protracted periods.

A significant limitation to nonparenteral administration of many peptides, particularly those of higher molecular weights, is that they are poorly absorbed across the mucosal membranes which line the exposed surfaces of the oral, rectal, and vaginal orifices, the cornea of the eye, and the gut; thus the bioavailability of peptides after nonparenteral administration to mucosal surfaces often is very low. Consequently, various types of absorption promoters have been investigated which are claimed to have peptide absorption-enhancing properties. However, a recognized problem with absorption promoters is that they can cause irritation or tissue damage at the site of administration.

Among numerous possible drug delivery systems, emulsions occasionally have been proposed as pharmaceutical formulations for administration of peptides and proteins. In most cases those emulsions may be characterized as water-in-oil microemulsions, which are thermodynamically stable and usually self-emulsifying; see Cho et al., WO 90/03164; Cho et al., WO 91/14454; Affinity, WO 92/18147; Riley, U.S. Pat. No. 5,055,303; Ritschel, *Meth. Find. Exp. Clin. Pharmacol.* 13: 205–220 (1991). In each of these cases, the internal dispersed phase containing the protein typically is aqueous and the continuous phase typically is lipoidal.

Other types of microparticulate drug delivery systems also have been proposed as suitable for oral administration of therapeutic proteins, such as microspheres (WO 93/00077), lipospheres (Domb, U.S. Pat. No. 5,188,837), microcapsules (EP 442671), liposomes (LTI, WO 91/05545), or other lipid vesicles (Yoshida et al., EPA 140,085). It has been postulated that particles in the appropriate submicron size range in and of themselves enhance transport through the intestinal mucosa. However, this hypothesis is disputed by other experts in delivery systems for biopharmaceuticals; see Davis, *J. Pharm. Pharmacol.* 44: 186–190, (1992).

Individually, various components of emulsions have been considered as candidates for improving bioavailability of peptides. Thus, oral lipid medicinal compositions have been disclosed (Liedtke, U.S. Pat. No. 5,120,710) utilizing a semi-solid lipid component combined with a solid water soluble component. Surfactants of many types have been utilized as promoters of peptide absorption (EP 115627; GB 2,127,689; and U.S. Pat. No. 4,548,922). However, such surfactants have deleterious effects on the intestinal mucosa and may not be safe for their designated purpose.

Emulsification with a natural emulsifier derived from mammalian milk has been suggested as a method to circumvent the utilization of harmful surfactants (Yoshiaki et al., EP 0 494 654). These emulsions are not produced in the highly relevant submicron size range; rather, particles below 1 μm are intentionally excluded.

Other emulsions have been disclosed in the submicron size range, but which necessarily contain specific ingredients such as lysophosphatidylcholine (Yesair, WO 92/03121).

Zerbe et al., WO 93/00076, disclose a drug delivery system consisting of a suspension of microparticles having a spherical core composed of a biopolymer, preferably a protein such as albumin or gelatin, which typically has been crosslinked or denatured to maintain its structural coherency. The spherical core may be combined with a bioadhesive polymer.

Riley, U.S. Pat. No. 5,055,303, discloses a bioadherent emulsion of the water-in-hydrophobic phase type, wherein the continuous hydrophobic phase is a solid fat. Bioadhesion is not attributed to a specific adherent component, but rather is apparently ascribable to the viscosity of the solid continuous phase.

3. SUMMARY OF THE INVENTION

The present invention provides emulsions comprising a plurality of submicron particles, a bioactive peptide, and an aqueous continuous phase or that effect enhanced oral bioavailability of the peptide. Another aspect of the invention provides compositions and methods of administering peptides in an emulsion comprising a plurality of submicron particles, a mucoadhesive macromolecule, a bioactive peptide, and an aqueous continuous phase, which promotes absorption of the bioactive peptide through mucosal surfaces by achieving mucoadhesion of the emulsion particles. Mucous surfaces suitable for application of the emulsions of the present invention may include corneal, conjunctival, buccal, sublingual, nasal, vaginal, pulmonary, stomachic, intestinal, and rectal routes of administration.

The emulsion particles have a hydrophobic core comprising a lipid or lipid-like composition. In certain embodiments, the emulsion is stabilized with amphiphilic and/or non-ionic surfactants.

A wide variety of bioactive peptides, including both water-soluble and water-insoluble peptides, may be accommodated in the present emulsions. The hydrophobic core and surfactant provide a microenvironment which accommodates membrane-associated peptide domains, while the aqueous continuous phase accommodates water-soluble peptide domains.

The term "peptide" herein includes both oligopeptides and proteins.

To facilitate intestinal absorption, the emulsions may be encapsulated in gelatin capsules or otherwise enterocoated to prevent their exposure to gastric fluids. Furthermore, the emulsions may be lyophilized as disclosed previously (Pharmos, PCT/US 93 01415) prior to their encapsulation in order to achieve added stability of the bioactive peptide.

5. DETAILED DESCRIPTION OF THE INVENTION

The present invention addresses the inherent problems in peptide delivery by formulating the peptides in an oil-in-water type submicron emulsion (SME) in which the mean particle size is in the range of 10 to 600 nm, more preferably 30 to 500 nm, commonly 50–300 nm. These formulations are suitable for administration by oral or rectal, vaginal, nasal, or other mucosal surface route. Moreover, bioadhesive polymers such as those currently used in pharmaceutical preparations optionally may be added to the emulsion to further enhance the absorption through mucous membranes.

Bioadhesive polymers optionally may be present in the emulsion. Use of bioadhesive polymers in pharmaceutical emulsions affords enhanced delivery of peptides in bioadhesive polymer-coated suspensions. Bioadhesive pharmaceutical emulsions: a) prolong the residence time in situ, thereby decreasing the number of peptide drug administrations required per day; and b) may be localized in the specified region to improve and enhance targeting and bioavailability of delivered peptides.

The ability to retain and localize a drug delivery emulsion in a selected region leads to improved bioavailability, especially for drugs exhibiting a narrow window of adsorption due to rapid metabolic turnover or quick excretion. Intimate contact with the target absorption membrane improves both the extent and rate of peptide absorption.

5.1. Features of the Emulsion Particles

The bioadhesive emulsions of the present invention comprise an aqueous continuous phase suspending a colloidal phase of submicron particles. The particles have a weighted average diameter of 10 to 600 nm, more preferably 30 to 500 nm, most preferably 70 to 300 nm. In many embodiments, the weighted average diameter will be less than 450 nm, 400 nm, 300 nm, or 200 nm. Usually the diameter will be greater than 40 nm or 50 nm, and frequently is greater than 70 nm. Often the above-stated upper and lower diameter ranges will include both the weighted average and at least one standard deviation of particle diameter.

The emulsion particle comprises a hydrophobic core, often including or even consisting essentially of triglyceride. Optionally other hydrophobic lipids may be used, including cholesterol or cholesteryl esters, paraffin, mineral oil, silicone oil, and waxes. In many embodiments, the core of the particles will be substantially free of protein other than the bioactive protein to be delivered, i.e., less than 1% (w/w), and in most cases less than 0.1% of other protein.

The emulsion usually further comprises at least one surfactant, which may be a natural biologically compatible surfactant such as phospholipid (e.g., lecithin) or a pharmaceutically acceptable nonnatural surfactant such as Tween-80. The surfactant assists in maintaining particles within the desired size range and preventing their aggregation.

In many embodiments the emulsion may be formed and stabilized in the substantial absence of one or more cosurfactants selected from the group consisting of an unhalogenated aliphatic C3–C6 alcohol, a free fatty acid, a mono- or di-glyceride, a polyglycerol fatty acid ester (e.g., Plurol), or a lysophosphatidyl choline. One or all of the above-named cosurfactants may comprise less than 5%, commonly less than 1%, and frequently less than 0.1% (w/w) relative to the weight of the hydrophobic core.

The emulsion optionally further comprises a bioadhesive, usually mucoadhesive, polymer. The polymer frequently may contain multiple carboxylic acid moieties, e.g., polyacrylates, alginic acid, hyaluronic acid, pectin, or carboxymethylcellulose. Polymers bearing polyamine groups also are capable of binding to mucin, e.g., chitosan. Certain mucin-binding polymers are uncharged, e.g., hydroxypropylmethyl cellulose.

In many cases, the bioadhesive polymer is believed to coat or form a layer on the outer surface of the particle core, possibly in association with the surfactant. Frequently the addition of the bioadhesive polymer increases the mean particle diameter of the emulsion, as may be seen, e.g., in Examples 3, 8–9, and 13 of copending application Ser. No. 08/106,262 filed Aug. 13, 1993. This result is consistent with the "coating" model of polymer-core interaction, since the added polymer layer would be expected to result in a greater diameter. However, in other cases the added polymer makes little difference in, or actually decreases, particle diameter; see, e.g., Examples 4–5, 6–7, 17, and 21 of copending application Ser. No. 08/106,262 filed Aug. 13, 1993. In these circumstances, the polymer may have surfactant as well as mucous-binding properties, thereby inserting itself deeply into the surfactant interface. In extreme cases, the polymer may be sufficiently surface-active to reduce the average hydrophobic core diameter by increasing the effective surfactant-to-lipid ratio.

Regardless of the detailed molecular structure of the polymer-particle association, emulsions combining hydrophobic core and bioadhesive polymer are within the scope of the invention.

The continuous phase of the emulsion is aqueous, and may contain salts, sugars, antioxidants, preservatives, microbicides, buffers, osmoticants, cryoprotectants, and other pharmaceutically useful additives or solutes.

The emulsion also contains a biologically active peptide. The active peptide may be hydrophilic, hydrophobic, or amphiphilic since the emulsion provides a biphasic microenvironment.

5.2. Composition of the Hydrophobic Core

A hydrophobic compound which is suitably nontoxic for administration to mucosal surfaces may be used as a component of the core. Examples include triglycerides, preferably of food grade purity or better, which may be produced by synthesis or by isolation from natural sources. Natural sources may include animal fat or vegetable oil, e.g., soy oil, a source of long chain triglycerides (LCT). Other triglycerides of interest are composed predominantly of medium length fatty acids (C10–C18), denoted medium chain triglycerides (MCT). The fatty acid moieties of such triglycerides may be unsaturated, monounsaturated or polyunsaturated; mixtures of triglycerides having various fatty acid moieties are acceptable. The core may comprise a single hydrophobic compound or a mixture of compounds.

Other hydrophobic compounds which may be used include silicone oil, mineral oil, paraffin, and aliphatic and aromatic esters of hydrophobic acids, e.g., isopropyl myristate, benzyl benzoate, and tocopherol acetate. The ester category includes waxes, which often are composed of fatty acid moieties esterified with aliphatic alcohols, including C2–C6 short chain alcohols and C8–C22 fatty alcohols.

Optionally the core may contain cholesterol or cholesteryl esters. In many embodiments, cholesteryl esters or cholesterol comprise less than 10%, 5%, 1%, or even 0.1% (w/w) of the total hydrophobic components of the core.

Considerations in choice of core material include low toxicity and irritancy, biocompatibility, stability, and high loading capacity for biologically active compounds of interest such as drugs. Preferred hydrophobic core components have molecular weights below about 5,000 Da, more preferably below about 2,000 Da, and most preferably below about 1,500 Da. An exception is provided by silicone oils, which remain useful at much higher molecular weights.

5.3. Compositions of Surfactant Component

Some embodiments of the invention provide an improved bioadhesive emulsion comprising incorporation of an amphiphilic and/or nonionic surfactant such as phosphatidylcholine, Tween, etc. The surfactant is believed in many embodiments to interact with the bioadhesive polymer to form a hydrated polymer film coating associated with the surfactant at the stabilized lipid/water interface surrounding the particle core.

Preferred compositions contain a surfactant component. The surfactant stabilizes the outer surface of the hydrophobic core component of the emulsion particles, thereby promoting a more uniform and manipulable particle size. Usually the surfactant is present in a proportion of 0.01% to 5% (w/w) of the emulsion, preferably 0.05% to 2%.

Typically, the weight percentage of surfactant relative to hydrophobic (oil or other lipid) component is from 0.2% to 50%, more preferably from 5% to 20%. Higher ratios of surfactant to core lipid tend to promote smaller particle core diameters.

Surfactants may be either natural compounds, such as phospholipids and cholates, or nonnatural compounds such as: polysorbates, which are fatty acid esters of polyethoxylated sorbitol (Tween); polyethylene glycol esters of fatty acids from sources such as castor oil (Emulfor); polyethoxylated fatty acid, e.g. stearic acid (Simulsol M-53); Nonidet; polyethoxylated isooctylphenol/formaldehyde polymer (Tyloxapol); poloxamers, e.g., poly(oxyethylene)poly(oxypropylene) block copolymers (Pluronic); polyoxyethylene fatty alcohol ethers (Brij); polyoxyethylene nonylphenyl ethers (Triton N); polyoxyethylene isooctylphenyl ethers (Triton X); and SDS. Mixtures of surfactant molecules, including mixtures of surfactants of different chemical types, are acceptable. Surfactants should be suitable for pharmaceutical administration and compatible with the peptide to be delivered.

Particularly suitable surfactants include phospholipids, which are highly biocompatible. Especially preferred phospholipids are phosphatidylcholines (lecithins), such as soy or egg lecithin. Other suitable phospholipids include phosphatidylglycerol, phosphatidylinositol, phosphatidylserine, phosphatidic acid, cardiolipin, and phosphatidylethanolamine. The phospholipids may be isolated from natural sources or prepared by synthesis. Phospholipid surfactants are believed usually to form a single monolayer coating of the hydrophobic core.

In certain embodiments, the emulsion may be limited in or substantially free of one or more cosurfactants selected from the group consisting of free fatty acids, mono- or di-glycerides (fatty acid mono- or diesters of glycerol), aliphatic C3–C6 monoalcohols (exclusive of, e.g., chlorobutanol or other haloalkyl alcohol preservative), polyglycerol fatty acid esters (Plurol), or lysophosphatidyl choline. In many embodiments, the particular limited cosurfactant from the above group may constitute less than 5%, usually less than 1%, often less than 0.1%, relative to the weight of hydrophobic core component. In some embodiments, one or more cosurfactants may be present.

5.4. Bioactive Peptides

A wide variety of bioactive peptides and proteins may be incorporated into the emulsions of the invention. As used herein, the term "peptide" may refer to both oligopeptides (chains of fewer than 50 peptide-linked amino acids) and to proteins (chains of greater than 50 peptide-linked amino acids), unless the specific context indicates otherwise.

Among the peptides or polypeptides suitable for incorporation into the emulsions are the following examples, listed by therapeutic category:

AIDS
    CD4 peptides
    CPF-DD
    Peptide T
    Vasoactive Intestinal Peptide
    Tetradecapeptide
    Protease inhibitors
Anemia
    Erythropoietin
Proteins
    Insulin
    Growth hormone
    Interferons
    Interleukins
    Clotting factors
    Growth factors
Allergy
    Pentigetide
    Histamine Releasing Peptide Antigen
    Vasoactive Intestinal Peptide Analog
Antiinflammatory
    Antiflammins
    Complement blockers
    Corticotropin Releasing Factor
    Interferon Gamma antagonists
    Interleukin 6 antagonists
    Kinin antagonists
    Lymphocyte adhesion blockers (corleukin, CY 725, CY 726)
    Pancreatic trypsin inhibitor
    Somatostatin
Neuropharmaceuticals
    Calcium channel peptide (antipsychotic)
    DEYE (antipsychotic)
    Ebiratide (memory enhancement)
    DGAVP (memory enhancement
    Opiate agonists (E-2078, DPDPE, Dynorphin A)
    Opiate antagonists
    Sleep inducing peptide
Bone
    Calcitonin
    PTH-releasing peptide
    Growth hormone releasing peptide Growth
  Growth hormone releasing peptide
  Growth hormone
Gynecology
  LHRH agonists
  LHRH antagonists
  HCG
Coagulation
  Anticoagulants:
  Hirudin and analogs
  Platelet aggregation inhibitors (applagin, corplatin, disintegrins, integrelin, leech peptides, viper venom polypeptides)
  Platelet adhesion inhibitors
  Coagulation protease inhibitors (inhibitors of factors VIIa, Xa, XIIa and thrombin)
  Kininogen-derived peptides
  Procoagulants:
  Desmopressin and analogs
Cancer
  Antistasin
  EGF receptor blockers
  Bestatin
  LHRH agonists (buserelin, goserelin, leuprolide)
  LHRH antagonists
  Melanoma receptor blockers
  TGF beta or TGF beta inhibitors
Cardiovascular
  Atrial natriuretic peptide and analogs
  Auriculin
  Atrial peptide clearance inhibitors
  Brain neuritic peptide
  Urodilatin
  Captopril (hypertension)
  ACE inhibitor peptide
  Renin Inhibitor

5.4.1. Other Protein Components

In certain preferred preparations, the lipid particles of the inventive emulsions do not incorporate certain peptides other than the bioactive peptide to be delivered, e.g., milk fat globule apolipoproteins or serum apolipoproteins such as apoB, apoAI, apoAII, or apoE. Lipid particles of the invention in certain preferred embodiments also are substantially free of intracellular marker proteins associated with the intracellular cytoskeleton (e.g., actin, myosin, troponin, tubulin, vimentin, and spectrin). Lipid particles which do not contain intracellular marker proteins are herein defined as "noncellular" particles, since they lack characteristic indicia of lipid particles present in or derived from cellular sources.

In some embodiments, the emulsion particles will be free or substantially free of the above or other nonbioactive proteins, i.e., less than 5%, usually less than 1%, and frequently less than 0.1% (w/w) protein relative to other particle components.

5.5. Bioadhesive Macromolecules

Emulsions of the present invention optionally may contain a bioadhesive macromolecule or polymer in an amount sufficient to confer bioadhesive properties. The bioadhesive macromolecule enhances the delivery of biologically active peptides on or through the target surface. The bioadhesive macromolecule may be selected from acidic nonnaturally occurring polymers, preferably having at least one acidic group per four repeating or monomeric subunit moieties, such as poly(acrylic)- and/or poly(methacrylic) acid (e.g., Carbopol, Carhomer), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral nonnaturally occurring polymers, such as polyvinylalcohol; or their mixtures. The ionizable polymers may be present as free acids, bases, or salts, usually in a final concentration of 0.01–0.5% (w/vol).

Bioadhesive macromolecules often form viscous solutions, in addition to possessing more specific mucin binding properties. These effects may be distinguished by comparing the degree of adhesion to a mucin surface of a solution prepared with the putative bioadhesive macromolecule versus a similar control emulsion prepared with a non-bioadhesive macromolecule of comparable viscosity: for example, a starch or dextran solution. At similar viscosities, the emulsion prepared with a bioadhesive macromolecule will bind to the mucin surface more strongly than will the control emulsion prepared with the "nonbinding" macromolecule such as starch. Preferably, the bioadhesive macromolecule will produce at least 25% greater mucin binding than the control emulsion, more preferably at least 50% greater, still more preferably at least 100% greater mucin binding than the control emulsion. Either binding to mucin per se or amount or biological effect of the drug delivered may be used as a measurement parameter for bioadhesion. This test may be used to distinguish preferred bioadhesive molecules.

As used herein, a polymer of an indicated monomeric subunit contains at least 75%, preferably at least 90%, and up to 100% of the indicated type of monomer subunit; a copolymer of an indicated type of monomeric subunit contains at least 10%, preferably at least 25% of that monomeric subunit.

A preferred bioadhesive macromolecule is the family of acrylic acid polymers and copolymers, (e.g., CARBOPOL™). These contain the general structure:

$$-[-CH_2-CH(COOH)-]-_n$$

One preferred group of polymers of acrylic acid is commercially available under the tradename Carbopol. Carbopol 934 is available in a pharmaceutical grade.

Preferred bioadhesive or mucoadhesive macromolecules have a molecular weight of at least 50 kDa, preferably at least 300 kDa, and most preferably at least 1,000 kDa. Favored polymeric ionizable mucoadhesive macromolecules have not less than 2 mole percent acidic groups (e.g., COOH, SO$_3$H) or basic groups (NH$_2$, NRH, NR$_2$), relative to the number of monomeric units. More preferably, the acidic or basic groups constitute at least 5 mole percent, more preferably 10 mole percent, and still more preferably at least 25 or even 50, up to 100 mole % relative to the number of monomeric units of the macromolecule.

Preferred macromolecules also are soluble in water throughout their relevant concentration range (0.01–0.5% w/vol).

Incorporation of the bioadhesive macromolecule into the emulsion is believed to result in spontaneous association of the macromolecule with, and coating of, the emulsion particles, as in represented diagrammatically in FIG. 1. However, the resulting emulsion is within the scope of the invention regardless of the details of the microscopic particle structure.

5.6. Aqueous Solution

The aqueous solution constituting the continuous phase usually contains a biologically compatible buffer. Since bioadhesion of polymers having acidic groups is more pronounced at lower pH, the buffer is usually adjusted to the pH range 3–7, usually pH 3.5– 6.5, more usually pH 4 to 6, frequently pH 4.5 to 5.5. Certain basic polymers having amine groups, such as chitosan, may be exposed to pH as low as 3 during preparation at the emulsion, although the usual pH range as administered is similar to or may be slightly higher than that for acidic polymers, i.e., pH 6–8.

Optionally, suitable chelating agents such as citric acid or EDTA may be present to minimize polyvalent or divalent cation binding to the acidic groups of the polymer. Other optional components may include, inter alia, antioxidants, antimicrobials, cryoprotectants, preservatives, salts, amino acids, and additives such as glycerol to adjust the solution tonicity.

In many embodiments, the aqueous solution is substantially free from sorbitol; i.e., the weight of sorbitol in the emulsion may be less than 10% (w/w) relative to the weight of hydrophobic core lipid, often less than 5%, commonly less than 1% or even 0.1%, and may be essentially absent. In many embodiments, the emulsion is also substantially free from phosphorylcholine, which, like sorbitol, may be limited to levels of 10%, 5%, 1%, or 0.1% (w/w) or less.

5.7. Dehydrated Emulsions

A further aspect of the invention provides dehydrated emulsions, made by dehydrating a bioadhesive emulsion of the type described herein. Dehydrated emulsions may be stored for prolonged periods with minimal degradation, then reconstituted with water shortly before use. Residual water content in the dehydrated emulsion is usually less than 5% (w/w), commonly less than 2%, and often less than 1%.

Dehydration may be performed by standard methods, such as drying under reduced pressure; when the emulsion is frozen prior to dehydration, this low pressure evaporation is known as lyophilization. Freezing may be performed conveniently in a dry ice-acetone or ethyl alcohol bath. The pressure reduction may be achieved conveniently with a mechanical vacuum pump, usually fitted with a liquid nitrogen cold trap to protect the pump from contamination. Pressures in the low millitorr range, e.g., 10–50 millitorr, are routinely achievable, but higher or lower pressures are sufficient.

A cryoprotectant or anticoalescent compound may be added to the emulsion prior to dehydration to inhibit flocculation and coalescence upon rehydration. The cryoprotectant may be of any type known in the art, including sugars and polysaccharides such as sucrose or trehalose, and nonnatural polymers such as polyvinylpyrrolidone. Cryoprotectants are usually present at less than 25%, commonly 10%, more commonly 5%, 4% (w/v) or less in the emulsion before lyophilization.

A preferred category of cryoprotectants is amino acids and oligopeptides. Preferred amino acids include valine, leucine, isoleucine, lysine, methionine, threonine, serine, arginine, alanine, glycine, histidine, proline, phenylalanine, taurine, and carnitine, although any of the other natural amino acids may also be present. Amino acids may be of either D or L configuration, or a mixture; the natural L form is preferred. Amino acids may be present as their salts or esters, and as mixtures of amino acids or as pure species.

A particularly preferred amino acid is glycine, which may be present either in pure form or as a component of a mixture, e.g., in an hydrolyzate of collagen or other glycine-rich protein.

Mixtures of oligopeptides, especially di- and tripeptides, are another preferred type of cryoprotectant. These may be prepared conveniently as partial protein hydrolyzates or enzymatic digests.

The cryoprotective amino acids or oligopeptides are generally present in the emulsion at a concentration of about 0.25 to 25% (w/w), preferably about 0.5 to 12% (w/w), more preferably about 1 to 10% (w/w), and commonly 3–6% (w/w).

Cryoprotectants and methods of making lyophilized emulsions are taught in more detail in copending application Ser. No. 08/016,913 filed Feb. 12, 1993 which is herein incorporated by reference.

5.8. Methods of Preparation

A further embodiment of the invention relates to methods for preparation of a bioadhesive emulsion whereby the pH of the aqueous emulsion containing the bioadhesive polymer and the hydrophobic phase is adjusted to a level which promotes substantial, i.e. at least 90%, preferably at least 99%, or essentially complete ionization of the polymer. Thereafter the pH may be readjusted to a second level to enhance biocompatability or mucin binding, or to provide a stable storage environment prior to use. This process may be accomplished during or after incorporation of the bioadhesive polymer into the water phase, followed by emulsification together with the oil phase; alternatively, the bioadhesive polymer in water solution may be added to a prepared emulsion.

Usually the hydrophobic phase is homogenized in an aqueous phase by a pressure homogenizer, which facilitates production of smaller particle diameters which fall within the stated size range of the emulsions.

The pH is considered "adjusted" in this contemplation when the bioadhesive polymer and formed emulsion coexist or are combined at the relevant pH, regardless of the manner or sequence of steps by which the relevant pH was achieved in the combined emulsion.

Figure 1A:
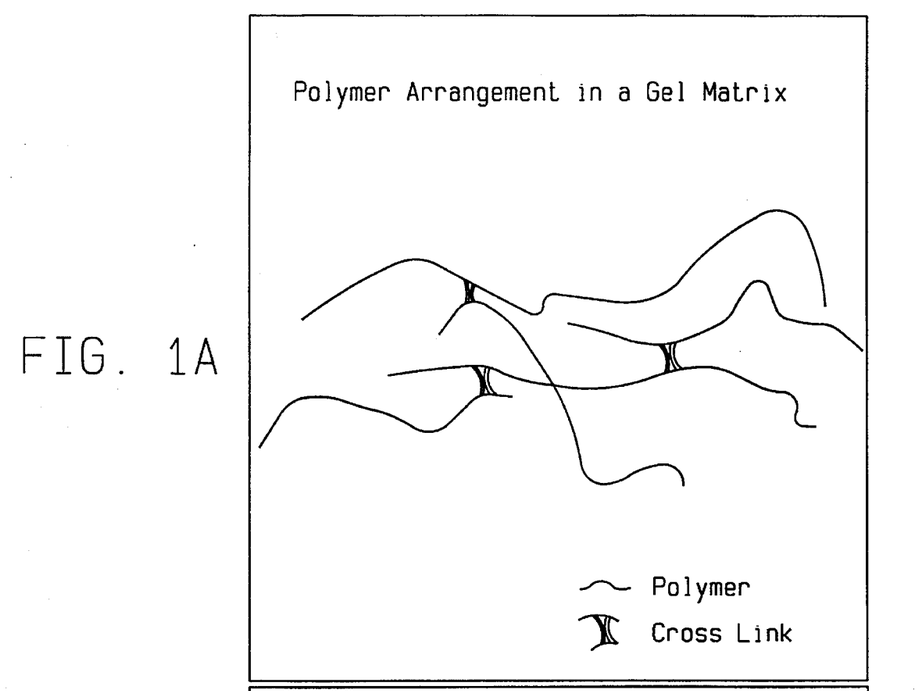
FIG. 1 illustrates some of the differences among a crosslinked polymer gel matrix (A), a conventional oil-in-water emulsion (B), an emulsion of oil droplets diffusing in a gel matrix (C), and bioadhesive coated emulsion particles of an aspect of the present invention (D).
Figure 1B:
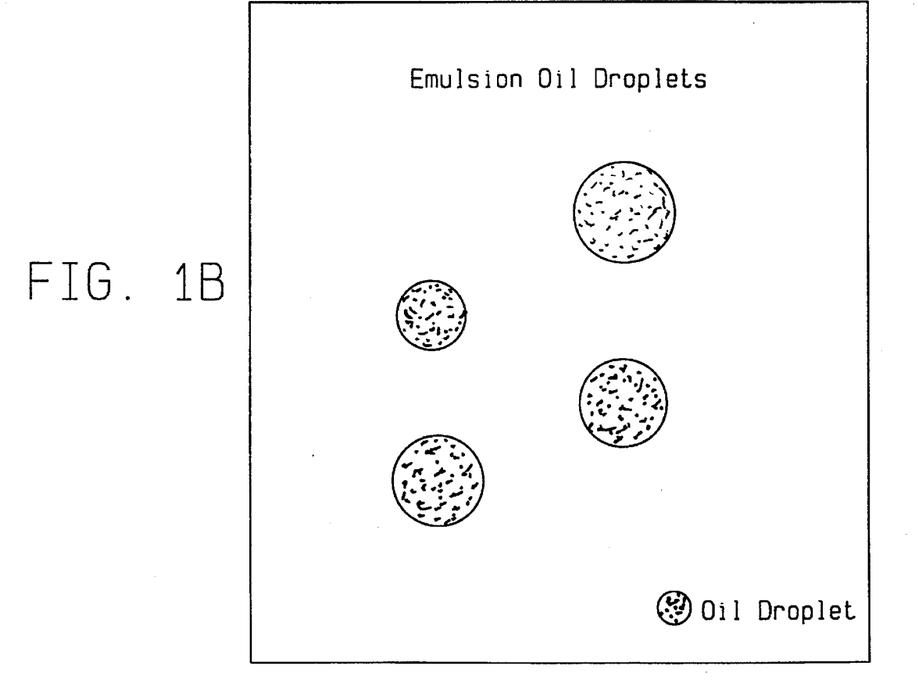
Figure 1C:
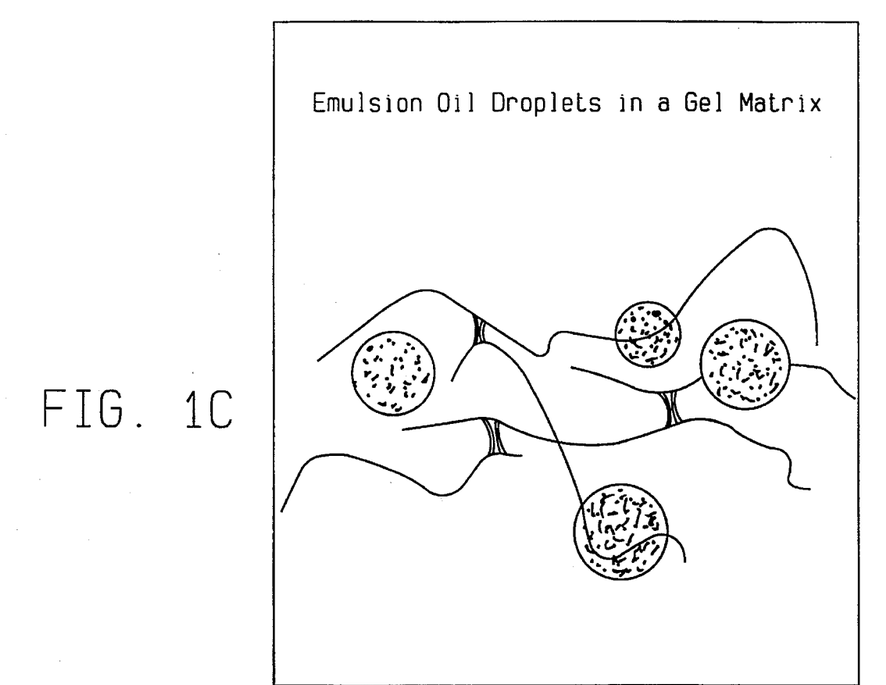
Figure 1D:
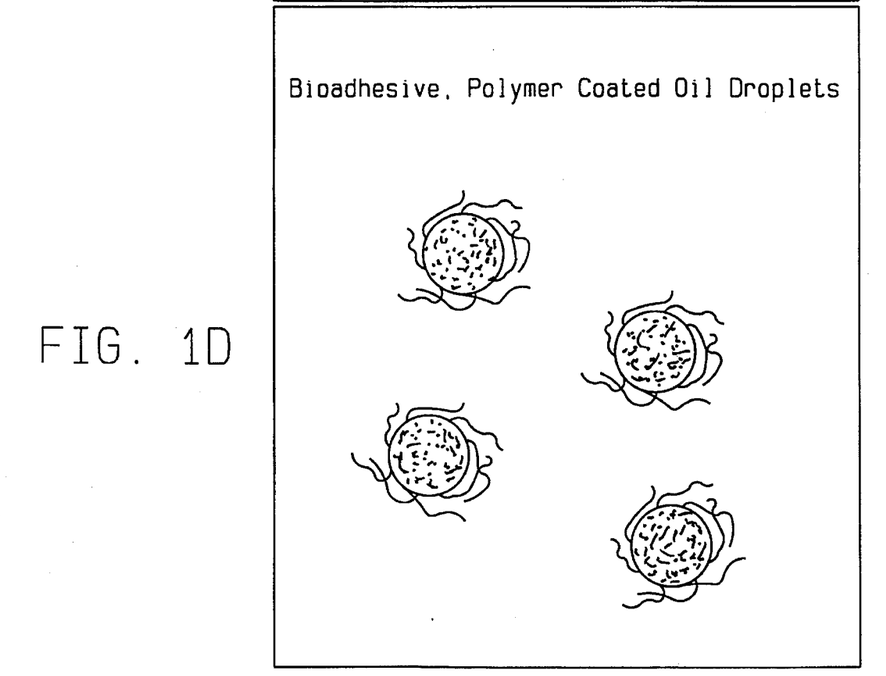
Figure 2:
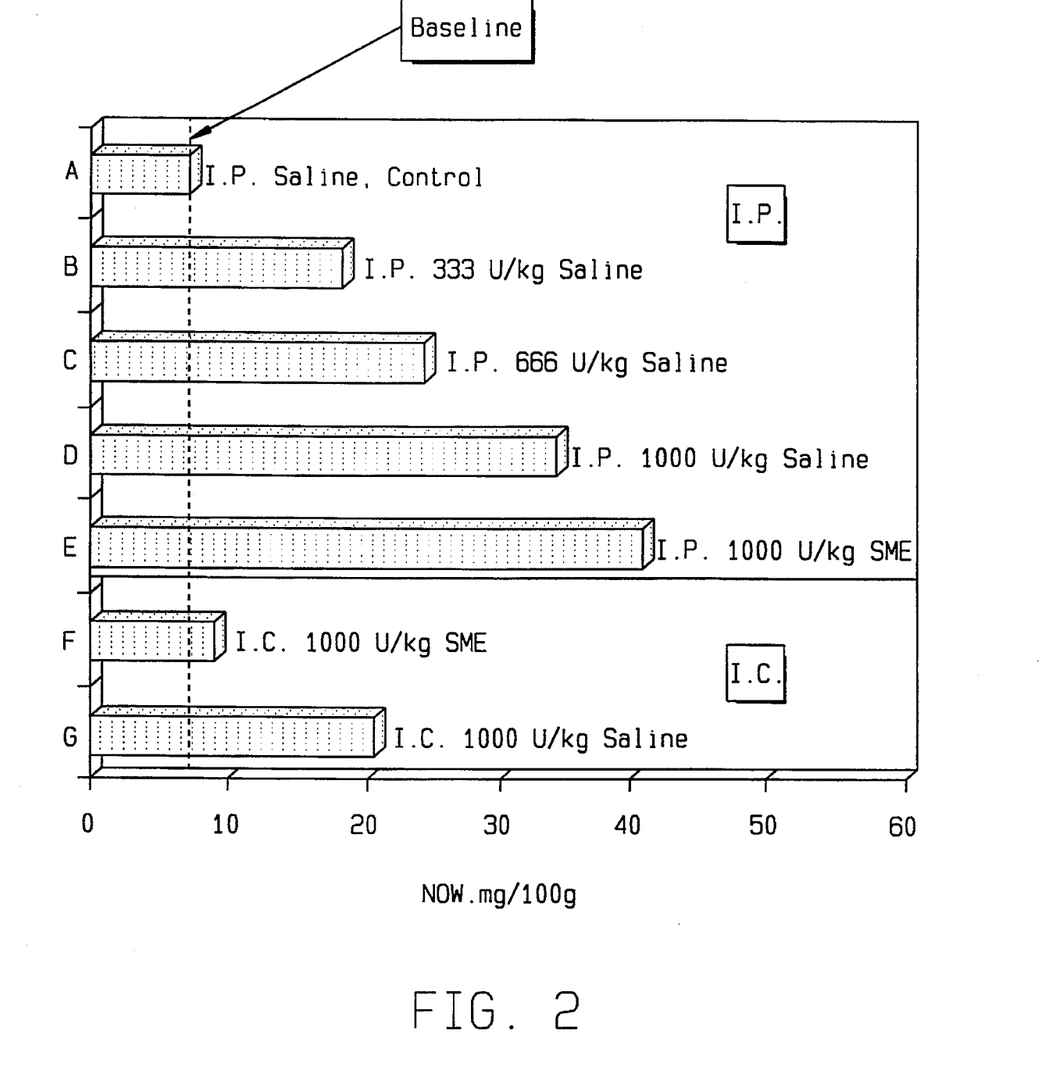
FIG. 2 is a graph showing the approximately linear dose-response curve for human chorionic gonadotropin (HCG) as measured by normalized ovary weight.

For polyanionic polymers, the pH is adjusted to an intermediate value not less than pKa+2, preferably pKa+3 or higher (in the range of 5.6–8.5 for polycarboxylic acid polymers), thereby producing substantial to essentially complete dissociation or ionization of the carboxylic acid groups; subsequently the pH of the final preparation is adjusted to 3–7, more commonly 3.5–6.0, to enhance the mucin-binding interaction. The pH profile obtained during one preparation by this procedure of an exemplary emulsion using Carbopol as the mucoadhesive polymer is shown in FIG. 2.

Although the pKa of a polyionic polymer is a sum of multiple pKas, the average pKa values for polymers are comparable to those for the corresponding monomeric structure.

In the case of polycationic polymers such as chitosan, the desired intermediate pH range will be at least pKa-2, preferably pKa-3 or less, corresponding even to pH below 3 for chitosan; the pH may be elevated to a more biologically compatible value, e.g. pH 6–8, after the final emulsion is formed.

When manufacture of emulsions with ionic bioadhesive polymers is attempted under other conditions not utilizing pH changes, bioadhesive polymers sometimes form a water-insoluble interpolymer complex with the surfactants, which leads to the breakdown of the emulsion.

6. EXAMPLE 1

HCG Delivery to the Colon

HCG, human chorionic gonadotropin, is a large molecular weight glycoprotein (about 27 kDa), currently administered only by i.m. injection. HCG is used to treat infertility, male hypogonadism and prepubertal cryptorchidism. HCG is obtained by extraction from urine.

6.1. Methods

HCG was administered in saline or submicron emulsion (SME), i.p. or i.c. (intracolonic) to anaesthetized Sprague-Dawley female prepubertal rats, 120 g. The rats were sacrificed four days post treatment and the reproductive organs weighed. The ovarian weight gain is a direct and ultimate pharmacological outcome of HCG treatment. Pharmacological effects after colonic administration of HCG in various vehicles was evaluated as PA%; this is defined as follows:

$$PA\% = \frac{(NOW_{ic}/D_{ic})}{(NOW_{iv}/D_{iv})} \times 100$$

where NOW is Normalized Ovarian Weight, D is the dose, ic indicates intracolonic administration, and iv intravenous administration.

6.2. Results

We have found that multiple administrations of HCG in SME to the colon of rats elicits significant effect on weight increase of the sex organs in amount comparable to systemic administration. Administration i.c. of HCG in SME was very effective, whereas administation i.c. in saline was not effective at all. Data in Table 1 refer to single dose administration and establishment of a dose response profile which enables evaluation of PA%.

Figure 3:
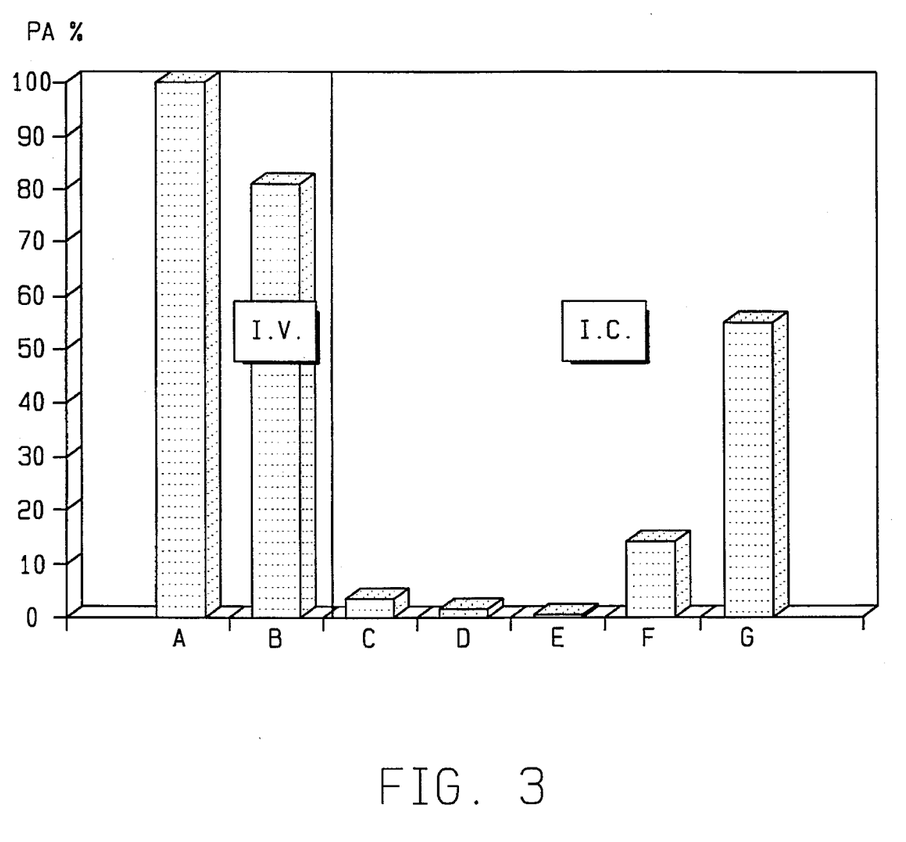
FIG. 3 is a bar graph showing relative PA% of formulations containing HCG, as administered i.p. or i.c.

FIG. 2 shows the linear relationship obtained between normalized ovarian weight gain and i.p. dose of HCG in saline (groups A–D). When 1000 U/kg were injected i.c. in saline, no ovarian weight gain was observed. However, 1000 U/kg of HCG formulated in SME and administered i.c., shows an effect approximately equivalent to 333 U/kg i.p., suggesting about 35% pharmacological equivalence; see FIG. 3. The actual calculated PA% for this group is 49%. As another control group, placebo SME was administered i.p.; this did not alter ovarian weight at all.

6.3 Discussion

HCG effect may be quantitatively estimated via ovarian weight linear response to the systemic dose administered. HCG in saline injected I.C. is apparently not absorbed since ovaries did not respond. This is in agreement with the well-documented poor oral absorption of peptides. However, HCG formulated in SME and administrated I.C., group G in Table 1, is absorbed in significant levels as concluded from the calculated high PA%, of more than 40%.

TABLE 1

Single Dose Administration of HCG and Establishment of Dose Response Profile for Evaluation of PA %

| Group | Route | Dose U/kg | Vehicle | No. of Animals | Ovary Weight mg/100 kg (NOW) | PA % | ME % |
|---|---|---|---|---|---|---|---|
| A | I.P. | 00 | Saline | 2 | 7.4 | 0 | 0 |
| B | I.P. | 333 | Saline | 2 | 18.3 | 120 | 147 |
| C | I.P. | 666 | Saline | 2 | 24.5 | 95 | 231 |
| D | I.P. | 1000 | Saline | 4 | 34.5 | 100a | 366 |
| E | I.P. | 1000 | SME | 4 | 41.1 | 124 | 455 |
| F | I.C. | 1000 | Saline | 4 | 9.0 | 5 | 22 |
| G | I.C. | 1000 | SME | 4 | 20.9 | 49 | 182 |

NOW = Normalized Ovary Weight to body weight, mg/100 g
a = Standard I.P. dose for PA % calculation, I.P. values are used instead of I.V.

6.4. Conclusion

Significant and unexpected pharmacological activity has been achieved with colonic HCG when formulated in SME.

7. EXAMPLE 2

Salmon Calcitonin in Carbopol Containing Submicron Emulsion, for Colonic Drug Delivery by Intestinal Bioadhesion An emulsion was prepared from 10.0 g MCT oil phase (90% MCT oil, 10% lecithin), 7.5 g polyethoxylated castor oil (Emulfor EL-620), and 482.5 g of water. All components were mixed by magnetic stirrer for 10 minutes, after which the coarse emulsion was dispersed by high-pressure homogenizer (Gaulion Microlab 70) at 700 bar, 8 cycles (10 minutes) at a temperature of no more than 40° C. Ninety-five g of the ready emulsion were mixed with 4000 international units of salmon calcitonin (as TFA salt, in 400 μl of water); 1.0 g polyvinylpyrrolidone K-10 and 4.0 g glycine were added as cryoprotectants. After complete dissolution, 5 ml of 1% Carbopol 940 in water was added. The pH was adjusted to 4.2, and the emulsion was freeze-dried. Mean oil droplet size was 76±27 nm before lyophilization, and 116±40 nm after reconstitution, using the Coulter N4MD particle size analyzer (Coulter Electronics, England).

A control sample was prepared in the same manner but without Carbopol. Mean oil droplet size (N4MD) was 49±23 nm before freeze-drying, 97±35 nm after reconstitution.

7.1. EXAMPLE 3

Improved Colonic Absorption of Calcitonin

Table 2 demonstrates improved colonic absorption of calcitonin in bioadhesive submicron emulsions. Calcitonin (salcatonin, Malinckrodt) was administered i.v. or i.c. to anesthetized Sabra rats (intracolonic) in saline solution, in SME, or in bioadhesive SME. All emulsions were lyophilized and reconstituted before use, due to the instability of calcitonin during storage. Blood samples were taken 10, 20, 30, 60, 120, 180 and 240 minutes after treatment via a permanent cannula; plasma samples were separated and stored at −20° C. Free $Ca^{+2}$ levels were determined by atomic absorption spectrometry.

Groups
  A. i.v. 0.4 mg/kg in saline
  B. i.v. 0.4 mg/kg in SME
  C. i.c. 1.66 mg/kg in saline
  D. i.c. 16.6 mg/kg in saline
  E. i.c. 83.3 mg/kg in saline
  F. i.c. 1.66 mg/kg in SME
  G. i.c. 1.66 mg/kg in Bioadhesive SME The pharmacological activity, denoted PA%, was used to evaluate the relative effect of various routes of administration and dose levels on blood calcium levels. PA% was calculated for the individual rats and the values presented are the mean of each group. PA% was calculated as follows:

$$PA\% = \frac{(AUC_{ic}/D_{ic})}{(AUC_{iv}/D_{iv})} \times 100$$

where AUC is the Area Under the Curve, showing the integrated optical density over time; D is the dose; ic indicates intracolonic administration, and iv intravenous administration. ME, the maximal effect, is calculated as the maximal decrease in basal $Ca^{+2}$ levels, expressed in percent.

TABLE 2

Improved Colonic Absorption of Calcitonin in Bioadhesive Emulsion

| Group | No. of Animals | PA % | Maximal Effect |
|---|---|---|---|
| A. I.V. 0.025 mg/kg in saline | 4 | 100 | 20 |
| B. I.V. 0.025 mg/kg in SME | 6 | 81 | 17 |
| C. I.C. 0.1 mg/kg in saline | 4 | 3.5 | 8 |
| D. I.C. 1.0 mg/kg in saline | 4 | 1.5 | 13 |
| E. I.C. 5.0 mg/kg in saline | 4 | 0.4 | 17 |
| F. I.C. 0.1 mg/kg in SME | 6 | 12.0 | 11 |
| G. I.C. 0.1 mg/kg in Bioadhesive SME | 18* | 55.0 | 22 |

*Three Groups of 6 (Repeated Experiments)

Figure 4:
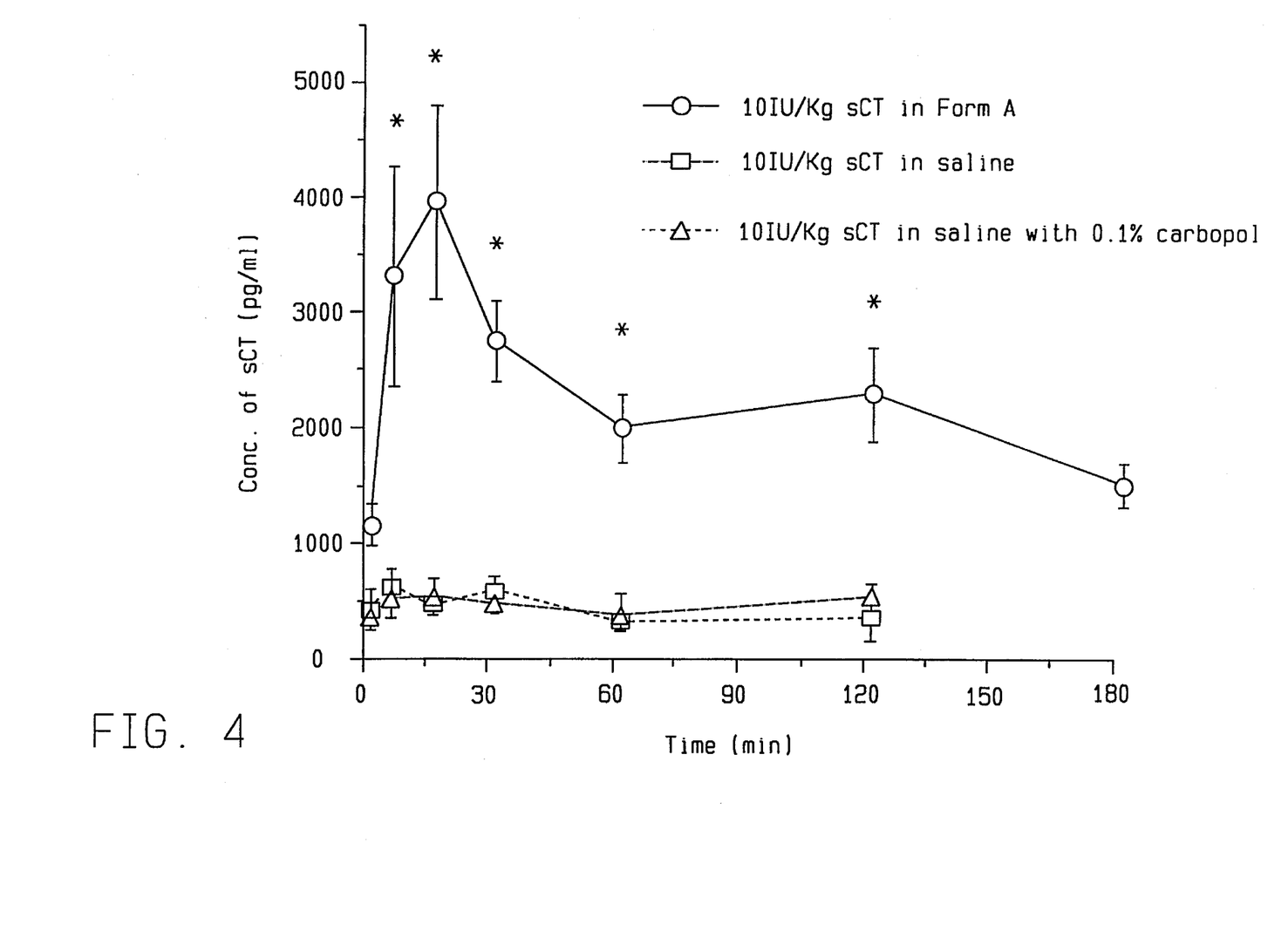
FIG. 4 is a bar graph showing relative PA% of formulations containing calcitonin, as administered i.v. or i.c.

FIG. 4 shows the PA% values for the various treatment groups. Group A was used to define 100% PA. Both SME preparations gave significant PA% values upon i.c. administration. Bioadhesive SME gave a significantly higher percent pharmacological activity than plain SME.

8.0. INCORPORATION BY REFERENCE

To the extent necessary to understand or complete the disclosure of the present invention, all publications, patents, and patent applications mentioned herein are expressly incorporated by reference therein to the same extent as though each were individually so incorporated.

What is claimed:

1. A lipid-in-water emulsion for administration of a biologically active peptide, said emulsion comprising a plurality of submicron particles each having a hydrophobic core, a surfactant, a biologically active peptide, and an aqueous continuous phase.

2. A lipid-in-water emulsion for administration of a biologically active peptide, said emulsion comprising a plurality of submicron particles each having a hydrophobic core, a surfactant, an aqueous continuous phase and a mucoadhesive macromolecule; wherein said hydrophobic core comprises a biologically active peptide.

3. The emulsion of claim 1 further comprising a mucoadhesive macromolecule selected from the group consisting of acidic naturally occurring polymers; acidic synthetically modified natural polymers; acidic nonnatural polymers; basic polymers; neutral nonnatural polymers; and neutral naturally occurring polymers.

4. The emulsion of claim 1 further comprising a mucoadhesive macromolecule selected from the group of acidic nonnatural polymers consisting of polymers and copolymers containing acrylic acid units, polymers and copolymers containing methacrylic acid units, and poly(methylvinylether/maleic anhydride) copolymer.

5. The emulsion of claim 4 wherein said polymer is polyacrylic acid.

6. The emulsion of claim 3 wherein said mucoadhesive macromolecule is carboxymethylcellulose.

7. The emulsion of claim 3 wherein said mucoadhesive macromolecule is hydroxypropylmethylcellulose.

8. The emulsion of claim 1 further comprising a mucoadhesive macromolecule of a naturally occurring acidic polymer selected from the group consisting of pectin, alginic acid, hyaluronic acid, gum tragacanth, and karaya gum.

9. The emulsion of claim 1 wherein said hydrophobic core comprises a triglyceride.

10. The emulsion of claim 1 wherein said hydrophobic core comprises paraffin or mineral oil.

11. The emulsion of claim 1 wherein said hydrophobic core comprises silicone oil.

12. The emulsion of claim 1 wherein said hydrophobic core comprises an ester of a fatty acid.

13. The emulsion of claim 1 wherein said hydrophobic core contains less than 1% (w/w) cholesterol.

14. The emulsion of claim 1 wherein said emulsion further comprises a cryoprotectant.

15. The emulsion of claim 14 wherein said cryoprotectant is an amino acid or oligopeptide.

16. The emulsion of claim 14 wherein said cryoprotectant is polyvinylpyrrolidone.

17. The emulsion of claim 1 wherein said surfactant is selected from the group consisting of phosphatidylcholine, phosphatidylethanolamine, phosphatidylserine, phosphatidylinositol, phosphatidylglycerol, cholates, phosphatidic acid, and cardiolipin.

18. The emulsion of claim 17 wherein said surfactant comprises phosphatidylcholine.

19. The emulsion of claim 1 wherein said surfactant is selected from the group consisting of fatty alcohols, polyethylene glycol esters of fatty acids, polyethoxylated fatty acids, polyethoxylated fatty alcohol ethers, polyethoxylated alkylphenyl ethers, SDS, polysorbates, and poloxamers.

20. The emulsion of claim 19 wherein said surfactant comprises a polyethylene glycol ester of a fatty acid.

21. The emulsion of claim 1 wherein said biologically active peptide is selected from the group consisting of pentigetide, histamine releasing peptide antigen, and vasoactive intestinal peptide.

22. The emulsion of claim 1 wherein said biologically active peptide is selected from the group consisting of antiflammins, complement blockers, corticotropin releasing factor, interferon gamma antagonists, interleukin 6 antagonists, kinin antagonists, lymphocyte adhesion blockers, and pancreatic trypsin inhibitor.

23. The emulsion of claim 1 wherein said biologically active peptide is selected from the group consisting of calcitonin, PTH-releasing peptide, insulin, human chorionic gonadotropin, human growth hormone, and growth hormone releasing peptide.

24. The emulsion of claim 1 wherein said biologically active peptide is selected from the group consisting of hirudin; platelet aggregation inhibitors; platelet adhesion inhibitors; coagulation protease inhibitors of factors VIIa, Xa, XIIa and thrombin; kininogen-derived peptides; and desmopressin.

25. The emulsion of claim 1 wherein said biologically active peptide is selected from the group consisting of antistasin, EGF receptor blockers, bestatin, LHRH agonists, LHRH antagonists, melanoma receptor blockers, and TGF beta.

26. The emulsion of claim 1, wherein said biologically active peptide is selected from the group consisting of atrial natriuretic peptide and analogs, auriculin, atrial peptide clearance inhibitors, brain natriuretic peptide, urodilatin, captopril, ACE inhibitor peptide, and renin inhibitor.

27. The emulsion of claim 1 wherein said biologically active peptide is erythropoietin or adrenocortico-tropic hormone.

28. The emulsion of claim 1 wherein said plurality of submicron particles have an average particle diameter of 30–500 nm.

29. The emulsion of claim 1 wherein said average particle diameter is 70–300 nm.

30. The emulsion of claim 1 wherein said emulsion contains less than 1% (w/w) of an unhalogenated aliphatic C3–C6 alcohol cosurfactant, relative to the weight of the hydrophobic core.

31. The emulsion of claim 1 wherein said emulsion contains less than 1% (w/w) of a monoglyceride cosurfactant, relative to the weight of the hydrophobic core.

32. The emulsion of claim 1 wherein said emulsion contains less than 1% (w/w) of a lysophosphatidylcholine cosurfactant, relative to the weight of the hydrophobic core.

33. The emulsion of claim 1 wherein said emulsion contains less than 1% (w/w) sorbitol, relative to the weight of the hydrophobic core.

34. The emulsion of claim 1 wherein said emulsion contains less than 1% (w/w) milk or serum apolipoprotein, relative to the weight of the hydrophobic core.

35. A dehydrated emulsion for administration of a biologically active peptide, comprising a plurality of submicron particles each having a hydrophobic core, said biologically active peptide, and a surfactant, whereby a submicron lipid-in-water emulsion is generated when water is added to said dehydrated emulsion.

36. A method for administering a bioactive peptide comprising applying to a mucosal surface a lipid-in-water emulsion comprising a plurality of particles each having a hydrophobic core, a bioactive peptide, a surfactant, and an aqueous continuous phase.

37. The method of claim 36 wherein said emulsion comprises a mucoadhesive molecule.

38. The emulsion of claim 2 wherein the peptide is calcitonin, the surfactant comprises a phospholipid and a non-ionic surfactant, and the mucoadhesive macromolecule contains acrylic or methacrylic acid units.

39. The emulsion of claim 38 wherein the surfactant comprises phosphatidylcholine and a polyethylene glycol ester of a fatty acid, and the mucoadhesive macromolecule is a carbomer.

* * * * *